(12) United States Patent
Tsunoda et al.

(10) Patent No.: US 7,754,934 B2
(45) Date of Patent: Jul. 13, 2010

(54) PROCESS FOR PRODUCING ETHYLENE AND PROPYLENE

(75) Inventors: Takashi Tsunoda, Kurashiki (JP); Mitsuhiro Sekiguchi, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 784 days.

(21) Appl. No.: 11/631,644

(22) PCT Filed: Jul. 15, 2005

(86) PCT No.: PCT/JP2005/013128

§ 371 (c)(1),
(2), (4) Date: Jan. 5, 2007

(87) PCT Pub. No.: WO2006/009099

PCT Pub. Date: Jan. 26, 2006

(65) Prior Publication Data
US 2007/0265482 A1 Nov. 15, 2007

(30) Foreign Application Priority Data

Jul. 16, 2004 (JP) .............................. 2004-209654

(51) Int. Cl.
*C07C 4/06* (2006.01)
(52) U.S. Cl. .................. 585/651; 585/324; 585/330; 585/653; 502/64; 208/73; 208/76; 208/113; 208/120.15
(58) Field of Classification Search .................. 585/324, 585/330, 651, 653; 502/64; 208/73, 76, 208/113, 120.15
See application file for complete search history.

(56) References Cited

U.S. PATENT DOCUMENTS

| 3,756,942 | A |   | 9/1973 | Cattanach |   |
|---|---|---|---|---|---|
| 4,527,001 | A |   | 7/1985 | Kaiser |   |
| 4,613,721 | A |   | 9/1986 | Kaiser |   |
| 5,026,935 | A |   | 6/1991 | Leyshon et al. |   |
| 5,043,522 | A |   | 8/1991 | Leyshon et al. |   |
| 5,968,342 | A | * | 10/1999 | Tsunoda et al. | ........ 208/120.15 |
| 6,307,117 | B1 |   | 10/2001 | Tsunoda et al. |   |

FOREIGN PATENT DOCUMENTS

| EP | 0 109 060 A1 | 5/1984 |
| EP | 0395345 A1 | 10/1990 |
| EP | 0421700 A1 | 4/1991 |
| GB | 2345294 A | 7/2000 |

(Continued)

OTHER PUBLICATIONS

Supplementary European Search Report issuing in related EP appl. No. 05766311.4 dated Oct. 8, 2009.

*Primary Examiner*—Glenn Caldarola
*Assistant Examiner*—Prem C. Singh
(74) *Attorney, Agent, or Firm*—Birch, Stewart, Kolasch & Birch, LLP

(57) ABSTRACT

A process for efficiently and stably producing ethylene and propylene which comprises bringing a hydrocarbon feedstock comprising at least one $C_{4-12}$ olefin into contact with a zeolite-containing catalyst to obtain a reaction mixture containing ethylene and propylene, separating the reaction mixture into a fraction comprising ingredients ranging from hydrogen to $C_3$ hydrocarbons and a fraction comprising $C_4$ and higher hydrocarbons, and recycling the $C_4$ and higher hydrocarbons as they are to a reactor.

14 Claims, 1 Drawing Sheet

FOREIGN PATENT DOCUMENTS

| | | |
|---|---|---|
| JP | 49-41322 A | 4/1974 |
| JP | 50-49233 A | 5/1975 |
| JP | 3-27327 A | 2/1991 |
| JP | 3-167136 A | 7/1991 |
| KR | 2001-0024221 A | 3/2001 |
| WO | WO 00/10948 A1 | 3/2000 |

* cited by examiner

PROCESS FOR PRODUCING ETHYLENE AND PROPYLENE

TECHNICAL FIELD

The present invention relates to a method of catalytic conversion of hydrocarbon starting materials. More particularly, it relates to a method of efficiently and stably producing ethylene and propylene useful as petroleum chemistry starting materials from olefinic hydrocarbon starting materials using specific zeolites, reaction conditions and specific reaction processes.

BACKGROUND ART

There are known many methods of catalytically converting hydrocarbon starting materials containing olefins using catalysts containing zeolite, and there are many reports on the method of producing ethylene and propylene by catalytic conversion.

JP-A-49-41322 discloses a method of conversion of a paraffin, olefin and/or cycloparaffin (naphthene) of 5 or more carbon atoms, to an aromatic hydrocarbon, ethylene and propylene using an H (proton) type ZSM-5 zeolite. However, according to this method, aromatic hydrocarbons are obtained in a relatively high yield, whereas yields of ethylene and propylene are low.

JP-A-50-49233 discloses a method of conversion of an olefin or paraffin of 2-4 carbon atoms to an aromatic hydrocarbon, ethylene and propylene using a proton type ZSM-5 zeolite. However, according to this method, the aromatic hydrocarbon is also obtained in a relatively high yield, but yields of ethylene and propylene are low.

U.S. Pat. Nos. 4,527,001 and 4,613,721 disclose methods of conversion of butene to ethylene and propylene using an aluminophosphate-based molecular sieve. However, yields of ethylene and propylene are also low in this method.

EPC Publication 0109060 discloses a method of conversion of an olefin of 4-12 carbon atoms to ethylene and propylene using an H type ZSM-5 zeolite having a molar ratio $SiO_2/Al_2O_3$ of 350 or higher under specific reaction conditions.

WO 2000/010948 discloses a method of conversion of an olefin of 4-12 carbon atoms to ethylene and propylene using a non-proton type ZSM-5 zeolite having a molar ratio $SiO_2/Al_2O_3$ of 200-5000 and containing a metal of Group IB.

In the method of converting an olefin of 4-12 carbon atoms to ethylene and propylene using a zeolite-containing catalyst, olefins of about 4-8 carbon atoms are obtained as reaction products in addition to ethylene and propylene. This is because the starting olefin is dimerized and decomposed by the catalyst to result in conversion to the composition which is close to the equilibrium composition under the reaction conditions. Therefore, in order to efficiently convert the starting olefin to ethylene and propylene, it is essential to efficiently recycle olefins of 4 or more carbon atoms in the reaction products to the reaction vessel by a simple method.

EPC Publication 0109060 describes a method of recycling to the reaction vessel the olefins of 4-8 carbon atoms obtained by removing aromatic hydrocarbons from the reaction products. Furthermore, WO 2000/010948 describes a method of recycling to the reaction vessel the olefins of 4-8 carbon atoms obtained by removing fractions having a boiling point higher than those of aromatic hydrocarbons of 8 carbon atoms from the reaction products. However, these methods require a plurality of separators for obtaining the recycling materials, which increases apparatus cost and operating cost. Thus, a simpler method has been demanded.

DISCLOSURE OF INVENTION

An object of the present invention is to provide an improved recycling process for attaining efficient and stable production of ethylene and propylene by obtaining recycling materials from reaction products by a simple process in a method of producing ethylene and propylene from a hydrocarbon starting material containing at least one olefin of 4-12 carbon atoms using a catalyst containing a medium pore diameter zeolite.

The inventors have conducted intensive research in an attempt to attain the above object. As a result, it has been unexpectedly found that in a method of obtaining a reaction mixture containing ethylene and propylene by contacting a hydrocarbon starting material containing an olefin of 4-12 carbon atoms with a specific zeolite-containing catalyst under specific conditions, even when the reaction mixture is separated into a fraction comprising hydrogen and a hydrocarbons of 3 or less carbon atoms and a hydrocarbon of 4 or more carbon atoms, and the hydrocarbon of 4 or more carbon atoms is used, as it is, as a recycling material (without removing heavy materials), a stable operation is possible without adverse effect on deterioration of the catalyst, and based on this finding, the present invention has been accomplished.

That is, the present invention relates to the following production methods.

(1) A method of producing ethylene and propylene which comprises contacting a hydrocarbon starting material containing 20% by mass or more of at least one olefin of 4-12 carbon atoms with a catalyst containing a medium pore diameter zeolites, the zeolite containing silver and substantially no protons, having a molar ratio $SiO_2/Al_2O_3$ of 200-5000 and selected from the group consisting of ZSM-5 type zeolites, in a reaction vessel under the conditions of a reaction temperature of 400-600° C., a partial pressure of the hydrocarbon starting material of 0.01-0.5 MPa and a weight hourly space velocity of 1-100 $hr^{-1}$ to carry out a catalytic conversion reaction of said at least one olefin of 4-12 carbon atoms, thereby obtaining a reaction mixture containing ethylene and propylene, separating the reaction mixture into a fraction A containing mainly hydrogen and hydrocarbons of 1-3 carbon atoms and a fraction B containing mainly at least one hydrocarbon of 4 or more carbon atoms, and separating ethylene and propylene from the fraction A, said method meeting the following requirements (i) and (ii):

(i) to satisfy $\Delta AROMA/P \leq 13$ $\Delta AROMA = AROMAout - AROMAin$ (AROMAin: percent by mass of aromatic hydrocarbon component of 6-8 carbon atoms in the hydrocarbon starting material at the inlet of the reaction vessel, AROMAout: percent by mass of aromatic hydrocarbon component of 6-8 carbon atoms in the reaction mixture at the outlet of the reaction vessel, P: partial pressure of the hydrocarbon starting material [MPa]); and (ii) to recycle 10-95% by mass of the fraction B to the reaction vessel and use it as the hydrocarbon starting material.

(2) A method described in the above (1), wherein the fraction A is separated into a fraction $A_1$ containing mainly hydrogen and a hydrocarbon of 1-2 carbon atoms and a fraction $A_2$ containing mainly hydrocarbons of 3 carbon atoms, and at least a part of the fraction $A_1$ is recycled to the reaction vessel and used as a part of the hydrocarbon starting material.

(3) A method described in the above (1), wherein 15-90% by mass of the fraction B is recycled to the reaction vessel and used as a part of the hydrocarbon starting material.

(4) A method described in the above (1), wherein the formula in the requirement (i) is $\Delta AROMA/P \leq 10$.

(5) A method of producing ethylene and propylene which comprises contacting a hydrocarbon starting material containing 20% by mass or more of at least one olefin of 4-12 carbon atoms with a catalyst containing a medium pore diameter zeolites, the zeolites containing silver and substantially no protons, having a molar ratio $SiO_2/Al_2O_3$ of 200-5000 and selected from the group consisting of ZSM-5 type zeolites, in a reaction vessel under the conditions of a reaction temperature of 400-600° C., a partial pressure of the hydrocarbon starting material of 0.01-0.5 MPa and a weight hourly space velocity of 1-100 $hr^{-1}$ to carry out a catalytic conversion reaction of said at least one olefin of 4-12 carbon atoms, thereby obtaining a reaction mixture containing ethylene and propylene, separating the reaction mixture into a fraction C containing mainly hydrogen and a hydrocarbon of 1-2 carbon atoms and a fraction D containing mainly at least one hydrocarbon of 3 or more carbon atoms, separating the fraction D into a fraction $D_1$ containing mainly hydrocarbons of 3 carbon atoms and a fraction $D_2$ containing mainly at least one hydrocarbon of 4 or more carbon atoms and separating ethylene and/or propylene from the fraction C and/or the fraction $D_1$, said method meeting the following requirements (i) and (ii):

(i) to satisfy $\Delta AROMA/P \leq 13$ $$\Delta AROMA = AROMAout - AROMAin$$

(AROMAin: percent by mass of aromatic hydrocarbon component of 6-8 carbon atoms in the hydrocarbon starting material at the inlet of the reaction vessel, AROMAout: percent by mass of aromatic hydrocarbon component of 6-8 carbon atoms in the reaction mixture at the outlet of the reaction vessel, P: partial pressure of the hydrocarbon starting material [MPa]); and (ii) to recycle 10-95% by mass of the fraction $D_2$ to the reaction vessel and use it as the hydrocarbon starting material.

(6) A method described in the above (5), wherein at least a part of the fraction C is recycled to the reaction vessel and used as a part of the hydrocarbon starting material.

(7) A method described in the above (5), wherein 15-90% by mass of the fraction $D_2$ is recycled to the reaction vessel and used as the hydrocarbon starting material.

(8) A method described in any one of the above (5), wherein the formula in the requirement (i) is $\Delta AROMA/P \leq 10$.

(9) A method described in any one of the above (1)-(8), wherein the reaction vessel is an adiabatic fixed bed reaction vessel.

(10) A method described in any one of the above (1)-(8), wherein the reaction temperature is 500-580° C., the partial pressure of the hydrocarbon starting material is 0.05-0.3 MPa and the weight hourly space velocity is 2-10 $hr^{-1}$.

(11) A method described in any one of the above (1)-(4), wherein a part of the fraction B is used as a part or all of the hydrocarbon starting material and is contacted with a medium pore diameter zeolite-containing catalyst containing at least one member selected from the group consisting of metals belonging to Group IIB, Group IIIB and Group VIII of the periodic table and compounds thereof at a temperature of 650° C. or less in a gaseous phase to obtain an aromatic hydrocarbon.

(12) A method described in the above (11), wherein in the case of using a part of the fraction B as a part of the hydrocarbon starting material, the fraction $A_1$ containing mainly hydrogen and hydrocarbons of 1-2 carbon atoms which is separated from the fraction A is further used as a part of the hydrocarbon starting material.

(13) A method described in any one of the above (5)-(8), wherein a part of the fraction $D_2$ is used as a part or all of the hydrocarbon starting material and is contacted with a medium pore diameter zeolite-containing catalyst containing at least one selected from the group consisting of metals belonging to Group IIB, Group IIIB and Group VIII of the periodic table and compounds thereof at a temperature of 650° C. or less in a gaseous phase to obtain an aromatic hydrocarbon.

(14) A method described in the above (13), wherein in the case of using a part of the fraction $D_2$ as a part of the hydrocarbon starting material, the fraction C is additionally used as a part of the hydrocarbon starting material.

ADVANTAGES OF THE INVENTION

According to the production method of the present invention, propylene and ethylene can be efficiently and stably produced from an olefinic hydrocarbon starting material.

BEST MODE FOR CARRYING OUT THE INVENTION

Figure 1:
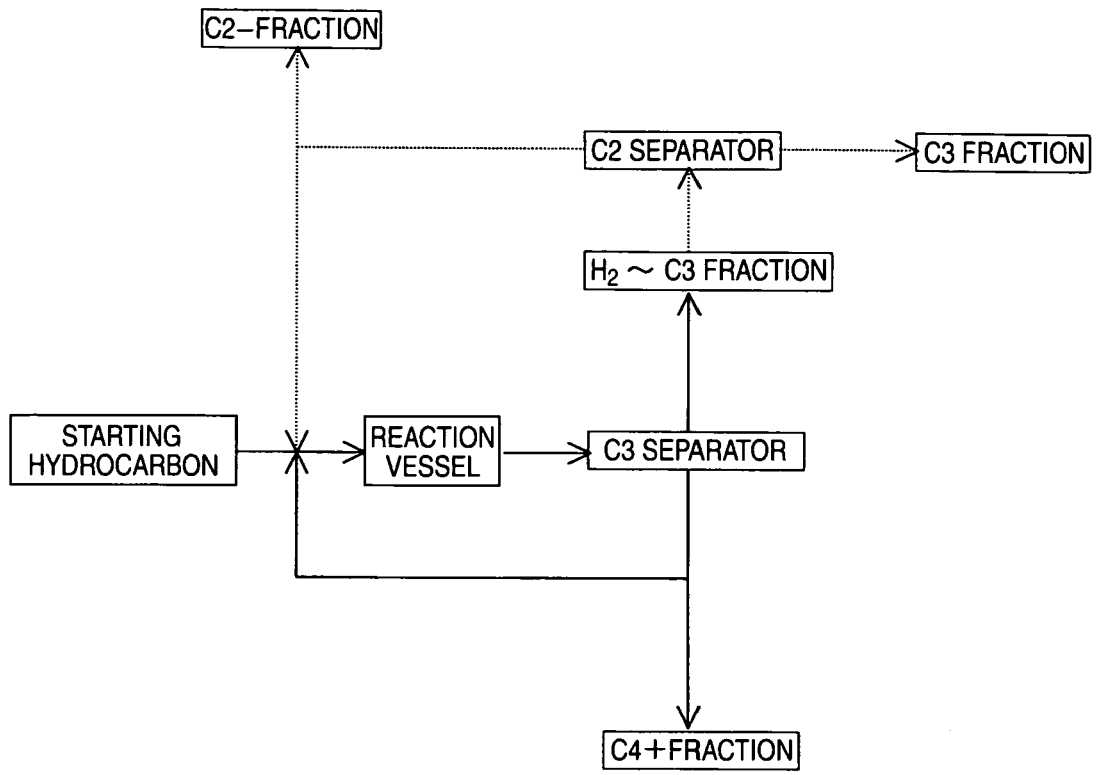
[FIG. 1] A flow sheet showing one embodiment of construction of the system used for producing ethylene and propylene according to the method of the present invention.

The present invention will be explained in detail below.

In the method of the present invention, a hydrocarbon starting material containing 20% by mass or more of at least one olefin of 4-12 carbon atoms is used as a starting material for producing ethylene and propylene.

The term "hydrocarbon starting material" in the present invention means a starting material containing mainly at least one material selected from the group consisting of hydrocarbons of 1-12 carbon atoms, such as normal paraffins, isoparaffins, olefins, cycloparaffins (naphthenes) and cycloparaffins having side chain alkyl groups.

In the method of the present invention, the hydrocarbon starting material contains at least one olefin of 4-12 carbon atoms in an amount of 20% by mass or more based on the mass of the hydrocarbon starting material.

The term "olefin" includes cycloparaffins in addition to the straight chain, branched chain and cyclic olefins.

If the content of the olefin in the hydrocarbon starting material is less than 20% by mass, yields of ethylene and propylene are insufficient. In the method of the present invention, the hydrocarbon starting material contains at least one olefin of 4-12 carbon atoms in an amount of preferably 30% by mass or more, more preferably 40% by mass or more and most preferably 50% by mass or more.

Furthermore, the hydrocarbon starting material may contain a small amount of an oxygen-containing compound such as tertiary butanol, methyl tert-butyl ether or methanol as an impurity. Moreover, the hydrocarbon starting material may contain a small amount of a diene or an acetylene such as methylacetylene, propadiene, butadiene or pentadiene. Due to their high reactivity, dienes and acetylenes accelerate deposition of carbonaceous materials (coking) on the surface of the catalyst. Therefore, during the conversion reaction continuously, the catalyst is deteriorated by the coking (deterioration with coking), resulting in deterioration in catalytic activity. There is no particular limitation in the content of dienes and acetylenes in the hydrocarbon starting material, but for the efficient and stable production of ethylene and propylene, the total concentration of dienes and acetylenes in the hydrocarbon starting material at the inlet of the reaction vessel is preferably 2% by mass or less, more preferably 1.5% by mass or less and especially preferably 1% by mass or less.

As preferred examples of the hydrocarbon starting material usable in the method of the present invention, mention may be made of the following hydrocarbons.

(1) A C4 fraction and a C5 fraction separated from products obtained by thermal cracking of petroleum hydrocarbons such as naphtha, and fractions obtained by partial hydrogenation of diolefins in the C4 and C5 fractions to olefins.

(2) A fraction obtained by separating and removing a part or all of butadiene and isobutene from the above C4 fraction.

(3) A fraction obtained by separating and removing a part or all of isoprene and cyclopentadiene from the above C5 fraction.

(4) A C4 fraction and/or gasoline fraction separated from products obtained by fluid catalytic cracking (FCC) of petroleum hydrocarbons such as reduced pressure distillated light oil.

(5) A C4 fraction and/or gasoline fraction separated from a coker.

(6) A C4 fraction and/or gasoline fraction separated from hydrocarbons synthesized from carbon monoxide and hydrogen by Fischer-Tropsch reaction (FT synthesis).

These may be used each alone or in a mixture of two or more.

According to the method of the present invention, the above hydrocarbon starting material is contacted with a specific zeolite-containing catalyst in a reaction vessel to carry out a catalytic conversion reaction of at least one olefin of 4-12 carbon atoms contained in the hydrocarbon starting material, thereby obtaining a reaction mixture containing ethylene and propylene, and ethylene and propylene are separated from the resulting reaction mixture.

In the method of the present invention, so-called "medium pore diameter zeolite" having a pore diameter of 5-6.5 Å is used as the zeolite in the above zeolite-based catalyst.

The term "medium pore diameter zeolite" means "a zeolite, the pore diameter of which lies between the pore diameter of small pore diameter zeolites such as A type zeolites and the pore diameter of large pore diameter zeolites such as mordenite and X type and Y type zeolites". The "medium pore diameter zeolites"0 have a so-called 10-membered oxygen ring in its crystal structure.

Examples of the medium pore diameter zeolites include ZSM-5, ZSM-8, ZSM-11, ZSM-12, ZSM-21, ZSM-23, ZSM-35, ZSM-38, etc. Of these zeolites, preferred are ZSM-5 type zeolites such as ZSM-5, ZSM-11 and ZSM-8, and ZSM-38. Furthermore, there may be used zeolites analogous to ZSM-5 and ZSM-11 which are disclosed in P. A. Jacobs and J. A. Martens, "Stud. Surf. Sci. Catal.", 33, P. 167-215 (1987, the Netherlands). Among them, ZSM-5 is especially preferred.

Moreover, in the method of the present invention, as the above zeolites, there may be used proton type zeolites or zeolites containing a metal belonging to Group IB of the periodic table and containing substantially no protons. Those which contain a metal belonging to Group IB of the periodic table and contain substantially no protons are particularly preferred.

Known methods can be used for obtaining proton type zeolites. That is, they can be prepared by a method of subjecting a zeolite obtained by hydrothermal synthesis, followed by drying and calcination to ion exchanging in an aqueous solution of nitric acid, hydrochloric acid or the like; a method of carrying out ion exchanging in an aqueous solution of an ammonium salt such as ammonium nitrate, ammonium chloride or the like to prepare an ammonium type zeolite, followed by drying and calcination to convert the zeolite to a proton type; a method of carrying out ion exchanging with a multivalent metal cation, and then calcining the zeolite; and the like.

The zeolite containing a metal belonging to Group IB of the periodic table and containing substantially no protons can be produced, for example, by the following methods.

The term "containing substantially no protons" in the present invention means that the amount of protons (amount of acid) in the zeolite measured by liquid phase ion exchanging/filtrate titration method explained below is 0.02 mmol or less per 1 gram of the zeolite. In the present invention, the amount of protons per 1 gram of the zeolite is more preferably 0.01 mmol or less.

The liquid phase ion exchanging/filtrate titration method is a method disclosed in Intrazeolite Chemistry, "ACS Symp. Ser.", 218, P 369-382 (1983, U.S.A.), Journal of the Chemical Society of Japan, [3], P. 521-527 (1989), etc. The measurement of the amount of protons using this method can be carried out in the following manner.

A zeolite calcined in air is subjected to ion exchange treatment using an aqueous NaCl solution, and then the zeolite is recovered by filtration and simultaneously a filtrate is obtained. The recovered zeolite is washed with pure water, and the resulting wash liquid is recovered in total and mixed with the above filtrate. The amount of protons in the mixed solution is measured by neutralization titration and this is referred to as the amount of protons in the zeolite.

It is known that ammonium ion type zeolites and multivalent metal cation type zeolites (for example, rare earth metal cation type zeolites) produce protons by heat treatment. Therefore, it is necessary to subject the zeolites to calcination treatment before the measurement of the amount of protons by the above method.

In the method of the present invention, a zeolite containing a metal belonging to Group IB of the periodic table (hereinafter referred to as "Group IB metal"), namely, at least one metal selected from the group consisting of copper, silver and gold, is used. As the Group IB metal, copper and silver are preferred and silver is especially preferred.

The "periodic table" in the present invention is the periodic table described in CRC Handbook of Chemistry and Physics, 75th edition [(David R. Lide, et al, published from CRC Press Inc. (1994-1995)), pages 1-15.

The term "containing Group IB metal" means containing a Group IB metal in the state of the corresponding cation. However, the Group IB metal may be contained in the zeolite in the state other than that of a cation in addition to being present in the state of cation. For example, it may be contained in the state of an oxide.

As examples of the method for containing the Group IB metal in the zeolite, mention may be made of, for example, a method of treating the zeolite by a known method such as an ion exchanging method, an impregnating method or kneading method, but preferably by the ion exchanging method.

When a Group IB metal is contained in the zeolite by the ion exchanging method, it is necessary to use a salt of the Group IB metal. Examples of the salt of the Group IB metal include silver nitrate, silver acetate, silver sulfate, copper chloride, copper sulfate, copper nitrate and gold chloride.

There is no severe limitation in the content of the Group IB metal, but the content is preferably 0.01-5% by mass, more preferably 0.02-3% by mass based on the mass of the zeolite. If the content of the Group IB metal is less than 0.01% by mass, catalytic activity of the zeolite-containing catalyst is insufficient, and even if it is added in an amount of more than 5% by mass, the performance of the zeolite-containing catalyst is usually not improved. The content of Group IB metal in the zeolite can be determined by known methods such as X-ray fluorescent analysis.

In the method of the present invention, it is essential that the molar ratio $SiO_2/Al_2O_3$ of the zeolite is 200 or more and 5,000 or less. If the molar ratio $SiO_2/Al_2O_3$ is less than 200, the zeolite-containing catalyst is apt to be deteriorated owing to coking caused by the conversion reaction. If the molar ratio $SiO_2/Al_2O_3$ exceeds 5000, the catalytic activity of the zeolite-containing catalyst is insufficient. The molar ratio $SiO_2/Al_2O_3$ of the zeolite is preferably 220 or more and 4,000 or less, more preferably 250 or more and 3,500 or less, most preferably 500 or more and 3,000 or less. The molar ratio $SiO_2/Al_2O_3$ of the zeolite can be determined by a known method, for example, by completely dissolving zeolite in an aqueous alkali solution and analyzing the resulting solution by plasma emission spectrochemical analysis or the like.

In the method of the present invention, it is also possible to use a metalloaluminosilicate in which a part of aluminum atoms constituting the zeolite skeleton are replaced with metals such as Ga, Fe, B and Cr or a metallosilicate in which all of the aluminum atoms constituting the zeolite skeleton are replaced with the metals mentioned above. In this case, the content of the above metals in the metalloaluminosilicate or metallosilicate is converted into the mol number of $Al_2O_3$ and then the molar ratio $SiO_2/Al_2O_3$ is calculated.

Furthermore, it is preferred that the zeolite additionally contains at least one metal selected from alkali metals and alkaline earth metals, more preferably at least one metal selected from alkali metals, further preferably at least one metal selected from the group consisting of sodium and potassium. In this case, the zeolite contains both the Group IB metal and at least one metal selected from alkali metals and alkaline earth metals.

As examples of the method for containing at least one metal selected from alkali metals and alkaline earth metals in the zeolite, mention may be made of the same methods as those for incorporating the Group IB metal in the zeolite.

The content of at least one metal selected from alkali metals and alkaline earth metals varies depending on the kind of the metals, and, for example, in the case of sodium, it is preferably 0.01-0.4% by mass based on the mass of the zeolite and in the case of potassium, it is preferably 0.01-0.8% by mass based on the mass of the zeolite. It is preferred that at least one metal selected from alkali metals and alkaline earth metals is contained in the state of the corresponding cation.

In preparing such zeolite, there are no particular limitations in the order and the number of times of the method of containing at least one metal selected from alkali metals and alkaline earth metals in the zeolite and the method of containing the Group IB metal. For example, the Group IB metal may be contained in the zeolite after at least one metal selected from alkali metals and alkaline earth metals is contained in the zeolite or at least one metal selected from alkali metals and alkaline earth metals may be contained in the zeolite after the Group IB metal is contained. In either case, however, it is preferred that the zeolite, in which the metals have been contained, contains substantially no protons as mentioned above.

If necessary, at least one metal selected from the group consisting of metals belonging to Groups IIb, III, Vb, VIb, VIIb and VIII, such as V, Cr, Mo, W, Mn, Pt, Pd, Fe, Ni, Zn and Ga, may be further contained in the zeolite-containing catalyst for purposes of inhibition of deterioration due to coking and improvement of the yield of ethylene and propylene.

The method for containing these metals is the same as the method for containing the Group IB metal, except that the kind of the metals used is different. The content of these metals is preferably 0.1-2% by mass based on the mass of the zeolite.

Furthermore, for the purpose of further improvement of resistance to deterioration due to coking, the zeolite-containing catalyst can be heat treated at a temperature of 500° C. or more in the presence of water vapor before contacting with the hydrocarbon starting material. The above heat treatment is preferably carried out under the conditions of a temperature of 500° C. or more and 900° C. or less and a partial pressure of water vapor of 0.01 atm or more.

When the zeolite-containing catalyst containing Group IB metal and containing substantially no proton is subjected to the above heat treatment, the heat treatment can also be carried out before the Group IB metal is contained in the zeolite. It is more preferred to carry out the heat treatment after the Group IB metal is contained in the zeolite.

In a case where the zeolite-containing catalyst is used for conversion reaction for a long period of time, deterioration due to coking may occur. In this case, the catalyst suffering from the coking deterioration can be regenerated by burning and removing the coke on the catalyst at a temperature of 400-700° C. usually in air or a mixed gas comprising oxygen and an inert gas. In this specification, such a treatment is called "regeneration treatment".

Because water vapor is produced in the regeneration treatment, the above heat treatment in the presence of water vapor can be carried out utilizing the produced water vapor. That is, by repeating the regeneration treatment of the zeolite-containing catalyst suffering from the coking deterioration caused by long-term use in conversion reactions, the same effect as that of the heat treatment can be attained.

Furthermore, if necessary, the zeolite used in the present invention can be used as a catalyst after subjected it to calcination. In this case, the calcination temperature is usually 500-900° C.

In using the zeolite-containing catalyst, it is preferred to make the zeolite-containing catalyst into a molded body to provide particles of proper shapes. In this case, only the zeolite is molded and the resulting molded body can be used as the zeolite-containing catalyst. However, ordinarily, the zeolite is mixed with a porous refractory inorganic oxide such as alumina, silica, silica/alumina, zirconia, titania, diatomaceous earth, or clay as a binder or molding diluent (matrix), the resulting mixture is molded and the resulting molded body is used as the zeolite-containing catalyst.

When the matrix or binder is used, the content thereof is preferably 10-90% by mass, more preferably 20-50% by mass based on the total mass of the zeolite and the matrix or binder.

According to the method of the present invention, by using the zeolite-containing catalyst mentioned above, in spite of using a hydrocarbon starting material containing an olefin in a high concentration of 20% by mass or more, coking deterioration of the zeolite-containing catalyst hardly occurs as compared with conventional methods. Therefore, it is not necessary to frequently repeat the regeneration operation. As a result, it becomes possible to stably and efficiently produce ethylene and propylene over a long period of time.

In the method of the present invention, a catalytic conversion reaction of at least one olefin of 4-12 carbon atoms is carried out in a reaction vessel by contacting the olefin with the above zeolite-containing catalyst. It is preferred to carry out the catalytic conversion reaction of the olefin of 4-12 carbon atoms under the following conditions where the olefin of 4-12 carbon atoms in the starting hydrocarbon is converted to ethylene and propylene at a high selectivity and paraffin coexisting in the starting hydrocarbon does not substantially react. That is, the reaction temperature is preferably 400-600° C., more preferably 500-580° C. The partial pressure of the hydrocarbon starting material is desirably lower, and is usually 0.01-0.5 MPa, preferably 0.05-0.3 MPa. The weight hourly space velocity WHSV of the hydrocarbon starting material with respect to the weight of the zeolite in the zeolite-containing catalyst is preferably 1-100 $hr^{-1}$, more preferably 2-10 $hr^{-1}$. The contact time of the hydrocarbon starting material with the zeolite-containing catalyst is preferably 5 seconds or less, more preferably 1 second or less.

Furthermore, the hydrocarbon starting material may be a mixture with a diluent gas. As the diluent gas, there may be used an inert gas such as hydrogen, methane, water vapor or nitrogen, but dilution with hydrogen is preferably not carried out. That is, hydrogen is used for inhibiting the deterioration of the catalyst due to coking. However, simultaneously, a hydrogenation reaction of the produced propylene or the like takes place, resulting in the adverse effect of reduction in propylene purity (propylene/(propylene+propane)). In the method of the present invention, coking deterioration of the catalyst is slight even without carrying out dilution with hydrogen, and stable operation can be performed. Thus, the dilution with hydrogen is preferably not carried out. (A small amount of hydrogen supplied to the reaction vessel by recycling of C2- fraction mentioned hereinafter, or the like, does not affect adversely as in the above-mentioned hydrogen for dilution.)

When the conversion reaction is carried out under the conditions where paraffin does not substantially react, the conversion reaction of olefin in the hydrocarbon starting material is selectively accelerated, and the conversion reaction of paraffin is suppressed. As a result, production of methane, ethane, propane, etc. by the conversion reaction of paraffin as by-products is inhibited, and separation and purification of ethylene and propylene from the reaction mixture can be easily performed.

The reaction vessel utilized in the method of the present invention for contacting the hydrocarbon starting material with the zeolite-containing catalyst may be any of fixed bed type, moving bed type, fluidized bed type and gas stream carrying type. The zeolite-containing catalyst used in the method of the present invention is hardly deteriorated by coking. Therefore, even when the fixed bed type reaction vessel is used, ethylene and propylene can be stably produced over a long period of time.

Furthermore, the conversion reaction of paraffin is a highly endothermic reaction, while the conversion reaction of olefin is a slightly endothermic reaction or an exothermic reaction though it depends on the reaction conditions. Therefore, when the olefin in the hydrocarbon starting material is selectively reacted under conditions where paraffin does not substantially react, it is not necessary to supply heat of reaction, and hence it is also possible to use a one-stage adiabatic fixed bed type reaction vessel having a simple structure.

Ethylene and propylene are separated from the reaction mixture containing ethylene and propylene which is obtained as above. Specifically, the first process comprises preferably separating the reaction mixture into a fraction A containing mainly hydrogen and hydrocarbons of 1-3 carbon atoms and a fraction B containing mainly at least one hydrocarbon of 4 or more carbon atoms, and separating ethylene and propylene from the fraction A. The second process comprises preferably separating the reaction mixture into a fraction C containing mainly hydrogen and hydrocarbons of 1-2 carbon atoms and a fraction D containing mainly at least one hydrocarbon of 3 or more carbon atoms, separating the fraction D into a fraction $D_1$ containing mainly a hydrocarbon of 3 carbon atoms and a fraction $D_2$ containing mainly at least one hydrocarbon of 4 or more carbon atoms, and separating ethylene and propylene from the fraction C and the fraction $D_1$. These separation steps can be carried out by combining various known processes such as fractional distillation and extraction.

As aforementioned, in the reaction mixture, olefins of 4 or more carbon atoms, aromatic hydrocarbons, etc. are present in addition to ethylene and propylene. Therefore, the effective utilization of the hydrocarbon starting material can be attained by using a so-called recycling reaction system which comprises separating all or a part of the olefins of 4 or more carbon atoms from the reaction mixture, recycling them to the reaction vessel and again reacting them.

In the method of the present invention, at least a part of the above fraction B or $D_2$ is recycled to the reaction vessel and is used as a part of the hydrocarbon starting material. That is, since the fraction B or $D_2$ is utilized, as it is, as a recycling material without carrying out purification, the simplest recycling process can be constructed.

In the method of the present invention, in order to efficiently obtain ethylene and propylene from the above-mentioned recycling process, it is preferred that $\Delta AROMA/P \leq 13$ is satisfied, and it is more preferred that $\Delta AROMA/P \leq 10$ is satisfied. Here, $\Delta AROMA = AROMAout - AROMAin$. AROMAout indicates the percent by mass of aromatic hydrocarbon component of 6-8 carbon atoms in the hydrocarbon starting material at the inlet of the reaction vessel, and AROMAout indicates the percent by mass of aromatic hydrocarbon component of 6-8 carbon atoms in the reaction mixture at the outlet of the reaction vessel. P means the partial pressure of the hydrocarbon starting material [MPa].

$\Delta AROMA$ is a yield [% by mass] of the aromatic hydrocarbon component of 6-8 carbon atoms produced in the reaction vessel. Therefore, the above formula shows that in order to efficiently obtain ethylene and propylene, it is desirable to inhibit the production of the aromatic hydrocarbon component of 6-8 carbon atoms as much as possible. Under the reaction conditions where the above formula is $\Delta AROMA/P > 13$, namely, aromatic hydrocarbons are readily produced, reduction of catalytic activity is apt to be caused by coking. Furthermore, due to the increase of the aromatic hydrocarbon component of 6-8 carbon atoms produced in the reaction vessel, the yields of ethylene and propylene decrease, and moreover, the proportions of the aromatic hydrocarbon component of 6-8 carbon atoms and a hydrocarbon component of 9 or more carbon atoms in the recycling material increase. As a result, there occur problems of accumulation in the reaction system and acceleration of coking.

The method for controlling the production of the aromatic hydrocarbon component of 6-8 carbon atoms in the present invention is not limited, and a method of reducing the conversion of olefin in the hydrocarbon starting material is generally employed. Here, the conversion of olefin means the olefin conversion on the basis of butene represented by the following formula.

Olefin conversion (%)={(concentration of olefin of 4 or more carbon atoms in hydrocarbon starting material at inlet of reaction vessel—concentration of butene in hydrocarbon component at outlet of reaction vessel)/concentration of olefin of 4 or more carbon atoms in hydrocarbon starting material at inlet of reaction vessel}×100.

The conversion of olefin is preferably 40-75% by mass.

The means for reducing the olefin conversion is also not limited, and includes, for example, increasing the weight hourly space velocity of the hydrocarbon starting material; lowering the reaction temperature; increasing the molar ratio $SiO_2/Al_2O_3$ of medium pore diameter zeolite in medium pore diameter zeolite-containing catalyst; and other methods. Moreover, in changing the zeolite, it is further preferred to use a zeolite containing a metal belonging to Group IB of the periodic table mentioned before and containing substantially no proton. This is because the zeolite inhibits production of the aromatic hydrocarbon of 6-8 carbon atoms more effectively than the conventional H type zeolite to make it possible to further increase the olefin conversion, and hence there is obtained the effect to increase yields of ethylene and propylene.

In the method of the present invention, the recycling ratio of the fraction B or $D_2$ is preferably 10-95% by mass, more preferably 15-90% by mass. If the recycling ratio is less than 10% by mass, the yields of ethylene and propylene are not sufficient. If the recycling ratio is more than 95% by mass, accumulation of the paraffin component contained in the starting hydrocarbon or the aromatic hydrocarbon component of 6-8 carbon atoms produced in the reaction vessel becomes conspicuous to excessively increase load on the reaction apparatus.

In the method of the present invention, the percent by mass of the hydrocarbon component of 9 or more carbon atoms in the fraction B or $D_2$ is preferably 20% by mass or less, more preferably 15% by mass or less. This is because ethylene and propylene cannot efficiently be obtained under the conditions where the percent by mass of the hydrocarbon component of 9 or more carbon atoms exceeds 20% by mass.

The method of the present invention will be explained in more detail taking the case of using as the hydrocarbon starting material a C4 fraction (fraction containing mainly hydrocarbons of 4 carbon atoms, such as butane, isobutane, butene and isobutene) obtained from a product of steam cracking of a petroleum hydrocarbon.

FIG. 1 shows one preferred embodiment of the recycle reaction system when the C4 fraction is used as the hydrocarbon starting material. A reaction mixture (a mixture of hydrogen and a hydrocarbon of 1 or more carbon atoms) is separated into a fraction containing mainly hydrogen and a hydrocarbon of 1-3 carbon atoms (hereinafter referred to as "$H_2$—C3 fraction") and a fraction containing mainly at least one hydrocarbon of 4 or more carbon atoms (hereinafter referred to as "C4+ fraction"). As the apparatus used for the separation (C3 separator), there may be used, for example, a distillation column, a flash drum (vapor-liquid separator), etc., and the distillation column is preferred. Ethylene and propylene are recovered from the resulting $H_2$—C3 fraction. On the other hand, at least a part of the C4+ fraction is recycled to the reaction vessel and utilized as a part of the starting material. By recycling the C4+ fraction, butane contained in the starting hydrocarbon is concentrated in the C4+ fraction. Therefore, when the total amount of the C4+ fraction is recycled, butane is accumulated, and hence accumulation of butane is controlled by recycling only a part of the resulting C4+ fraction to the reaction vessel.

Furthermore, the $H_2$—C3 fraction may be separated into a fraction containing mainly hydrogen and a hydrocarbon of 1-2 carbon atoms (hereinafter referred to as "C2− fraction") and a fraction containing mainly a hydrocarbon of 3 carbon atoms (hereinafter referred to as "C3 fraction"). As the apparatus used for separation (C2 separator), there may be used, for example, a distillation column, a flash drum (vapor-liquid separator), etc., and the distillation column is preferred. When propylene is selectively produced, at least a part of the C2− fraction is recycled to the reaction vessel and ethylene in the C2− fraction can be utilized as a part of the starting material. Since the C2− fraction contains hydrogen, methane and ethane in addition to ethylene, hydrogen, methane and ethane are accumulated if the total amount of the C2− fraction is recycled. Therefore, accumulation of hydrogen, methane and ethane is controlled by recycling only a part of the resulting C2− fraction to the reaction vessel. On the other hand, propylene is recovered from the C3 fraction, and this propylene can be utilized, as it is, as propylene of chemical grade in case the reaction conditions and separation conditions are properly set.

If necessary, the C4+ fraction can be separated into a fraction containing mainly a hydrocarbon of 4 carbon atoms (hereinafter referred to as "C4 fraction") and a fraction containing mainly at least one hydrocarbon of 5 or more carbon atoms (hereinafter referred to as "C5+ fraction"). The position of separation of the C4 fraction from the C4+ fraction may be either before or after recycling of the C4+ fraction. As the apparatus used for separation (C4 separator), there may be used, for example, a distillation column, a flash drum (vapor-liquid separator), etc., and the distillation column is preferred. At least a part of the resulting C4 fraction and/or C5+ fraction is recycled to the reaction vessel and can be used as a part of the starting hydrocarbon.

Figure 2:
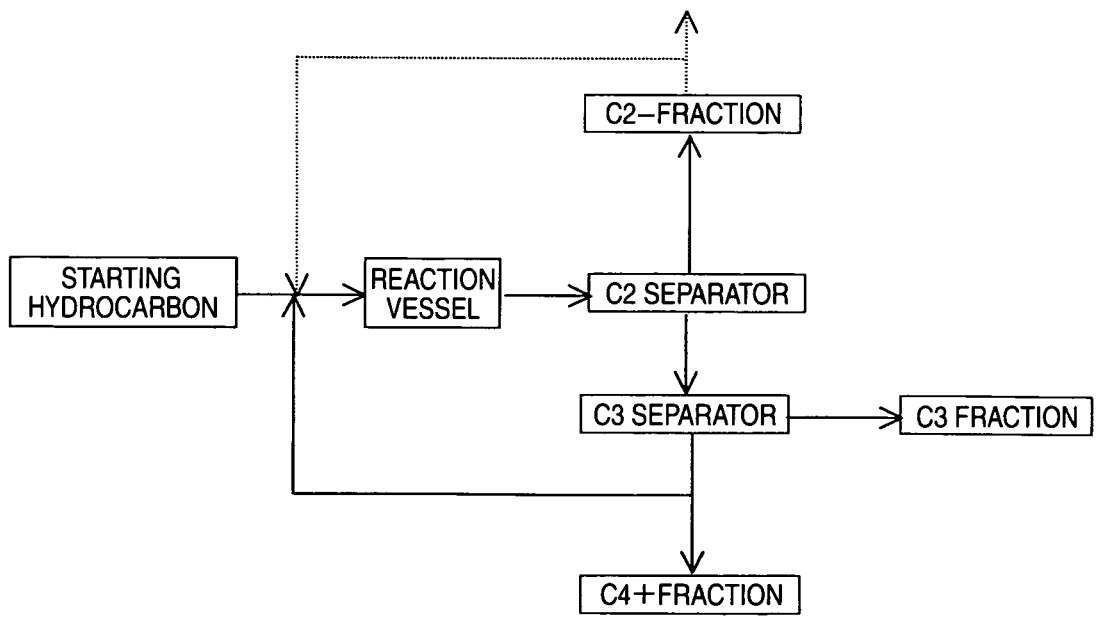
[FIG. 2] A flow sheet showing another embodiment of construction of the system used for producing ethylene and propylene according to the method of the present invention.

FIG. 2 shows another preferred embodiment of the recycle reaction system when the C4 fraction is used as the hydrocarbon starting material. A reaction mixture (a mixture of hydrogen and a hydrocarbon of 1 or more carbon atoms) is separated into a fraction containing mainly hydrogen and a hydrocarbon of 1-2 carbon atoms (hereinafter referred to as "C2− fraction") and a fraction containing mainly at least one hydrocarbon of 3 or more carbon atoms (hereinafter referred to as "C3+ fraction"). As apparatus used for separation (C2 separator), there may be used, for example, a distillation column, a flash drum (vapor-liquid separator), etc., and the distillation column is preferred. Ethylene is recovered from the resulting C2− fraction. When propylene is selectively produced, at least a part of the C2− fraction is recycled to the reaction vessel and ethylene in the C2− fraction is utilized as a part of the starting material as aforementioned.

On the other hand, the C3+ fraction is separated into a fraction containing mainly a hydrocarbon of 3 carbon atoms (hereinafter referred to as "C3 fraction") and a fraction containing mainly at least one hydrocarbon of 4 or more carbon atoms (hereinafter referred to as "C4+ fraction"). As the apparatus used for separation (C3 separator), there may be used, for example, a distillation column, a flash drum (vapor-liquid separator), etc., and the distillation column is preferred. Propylene is recovered from the C3 fraction, and this propylene can be utilized, as it is, as propylene of chemical grade in case the reaction conditions and separation conditions are properly set.

On the other hand, at least a part of the C4+ fraction is recycled to the reaction vessel and utilized as a part of the starting material. By recycling the C4+ fraction, butane contained in the starting hydrocarbon is concentrated in the C4+ fraction. Therefore, when the total amount of the C4+ fraction is recycled, butane is accumulated, and hence accumulation of butane is controlled by recycling only a part of the resulting C4+ fraction to the reaction vessel. As explained above on FIG. 1, if necessary, the C4+ fraction can be separated into a fraction containing mainly a hydrocarbon of 4 carbon atoms (hereinafter referred to as "C4 fraction") and a fraction containing mainly at least one hydrocarbon of 5 or more carbon atoms (hereinafter referred to as "C5+ fraction"). The position of separation of the C4 fraction from the C4+ fraction may be either before or after recycling of the C4+ fraction. As the apparatus used for separation (C4 separator), there may be used, for example, a distillation column, a flash drum (vapor-liquid separator), etc., and a distillation column which is preferred. At least a part of the resulting C4 fraction and/or C5+ fraction is recycled to the reaction vessel and can be used as a part of the starting hydrocarbon.

In the method of the present invention, yields of ethylene and propylene per the hydrocarbon starting material can be improved by carrying out in parallel the production of ethylene and propylene by the catalytic conversion mentioned above and the production of ethylene and propylene by steam cracking method (tube type thermal cracking method). In this case, since production of by-products such as methane can be inhibited, purification of ethylene and propylene can be efficiently performed. As an example of such method, mention may be made of a method which comprises feeding the fraction B or $D_2$ to a tube type cracking furnace to carry out steam cracking to obtain a steam cracking product containing ethylene and propylene and separating ethylene and propylene from the resulting steam cracking product. This steam cracking is carried out preferably under the conditions of 750-850° C. in temperature of the tube type cracking furnace, 0-15 kg/cm²G in pressure, 0.1-0.8 second in residence time and 0.1-1 in weight ratio of steam/hydrocarbon.

[Catalytic Cyclization Reaction]

In another embodiment of the method of the present invention, a part of the fraction B or the fraction $D_2$ is used as a part or all of the hydrocarbon starting material and is contacted with the medium pore diameter zeolite-containing catalyst, whereby an aromatic hydrocarbon of 6-9 carbon atoms can be obtained. In this specification, this reaction is referred to as "catalytic cyclization reaction". In the catalytic cyclization reaction, as the hydrocarbon starting material capable of being added to the fraction B or D2, mention may be made of, for example, a starting material containing mainly at least one material selected from the group consisting of hydrocarbons of 1-12 carbon atoms, such as normal paraffins, isoparaffins, olefins, cycloparaffins (naphthenes) and cycloparaffins having side chain alkyl group.

Furthermore, the hydrocarbon starting material used for the catalytic cyclization reaction may contain as impurities a small amount of oxygen-containing compounds such as tertiary butanol, methyl tertiary butyl ether, methanol, etc. Moreover, it may contain a small amount of a diene or acetylene such as methylacetylene, propadiene, butadiene, pentadiene, etc.

Examples of preferred hydrocarbon starting materials which can be added to the fraction B or $D_2$ in the catalytic cyclization reaction are the following materials as aforementioned.

(1) A C4 fraction and C5 fraction separated from products obtained by thermal cracking of petroleum hydrocarbons such as naphtha and fractions obtained by partial hydrogenation of diolefins in the C4 fraction and the C5 fraction to olefins.

(2) A fraction obtained by separating and removing a part or all of butadiene and isobutene from the above C4 fraction.

(3) A fraction obtained by separating and removing a part or all of isoprene and cyclopentadiene from the above C5 fraction.

(4) A C4 fraction and/or gasoline fraction separated from products obtained by fluid catalytic cracking (FCC) of petroleum hydrocarbons such as reduced pressure distillated light oil.

(5) A C4 fraction and/or gasoline fraction separated from a coker.

(6) A C4 fraction and/or gasoline fraction separated from hydrocarbons synthesized from carbon monoxide and hydrogen by Fischer-Tropsch reaction (FT synthesis).

These may be used each alone or in a mixture of two or more.

The zeolites used in the catalytic cyclization reaction are so-called "medium pore diameter zeolites" having a pore diameter of 5-6.5 Å. The meaning and examples of the term "medium pore diameter zeolites" are the same as aforementioned.

Furthermore, the medium pore diameter zeolite-containing catalyst used for the catalytic cyclization reaction can be made more suitable by adding thereto a hydrogenation/dehydrogenation metal component. Particularly, when at least one material selected from metals belonging to Group IIB, Group IIIB and Group VIII of the periodic table and compounds thereof, the zeolite-containing catalyst is improved in dehydrogenation cyclization ability and can be a suitable catalyst for producing aromatic hydrocarbons. The metals belonging to Group IIB, Group IIIB and Group VIII of the periodic table and compounds thereof are preferably zinc, gallium, indium, nickel, palladium, and platinum, and oxides and composite oxides thereof, and more preferably zinc, zinc oxide and composite oxides of zinc such as zinc aluminate. The amount of the metals belonging to Group IIB, Group IIIB and Group VIII of the periodic table and compounds thereof with respect to the zeolite-containing catalyst is preferably 0.1-20% by mass in terms of metal.

As the zeolite contained in the medium pore diameter zeolite-containing catalyst, there can be used proton type zeolite or a zeolite containing a Group IB metal, namely, at least one metal selected from the group consisting of copper, silver and gold. As the Group IB metal, copper and silver are preferred and silver is especially preferred. The method for obtaining the proton type zeolite and the method for containing the Group IB metal in the zeolite are the same as mentioned hereinbefore.

There is no severe limitation on the content of the Group IB metal, but the content is preferably 0.1-10% by mass, more preferably 0.2-5% by mass based on the mass of the zeolite. If the content of the Group IB metal is less than 0.1% by mass, the activity for the catalytic cyclization reaction is insufficient, and even if it is added in an amount exceeding 10% by mass, the performance is no longer improved.

The molar ratio $SiO_2/Al_2O_3$ of the zeolite in the catalytic cyclization reaction must be 20 or more from the point of view of stability as a catalyst. The upper limit of the molar ratio $SiO_2/Al_2O_3$ is not particularly restricted, and a zeolite of about 20-500, preferably about 28-300 in molar ratio $SiO_2/Al_2O_3$ is generally used.

In the catalytic cyclization reaction, it is also possible to use a metalloaluminosilicate in which a part of aluminum atoms constituting the zeolite skeleton are replaced with metals such as Ga, Fe, B and Cr or a metallosilicate in which all of the aluminum atoms constituting the zeolite skeleton are replaced with the above metals. In this case, the content of the above metals in the metalloaluminosilicate or metallosilicate is converted into terms of the mol number of $Al_2O_3$ and then the molar ratio $SiO_2/Al_2O_3$ is calculated.

Containing of alkali metal and alkaline earth metal in the zeolite and heat treatment of the zeolite in the presence of water vapor in the catalytic cyclization reaction are the same as aforementioned.

In a case where the zeolite-containing catalyst is used for the catalytic cyclization reaction for a long period of time, deterioration due to coking may sometimes occur. In this case, the catalyst deteriorated by coking can be regenerated by burning and removing the coke on the catalyst at a temperature of 400-700° C. usually in air or a mixed gas comprising oxygen and an inert gas. Because water vapor is produced in the regeneration treatment, the above heat treatment in the presence of water vapor can also be carried out utilizing the produced water vapor. That is, by repeating the regeneration treatment of the zeolite-containing catalyst used for the catalytic cyclization reaction for a long time and deteriorated by coking, the same effect as of the heat treatment can be attained.

Furthermore, if necessary, the zeolite used in the catalytic cyclization reaction can be used as a catalyst after being subjected to calcination. In this case, the calcination temperature is usually 500-900° C.

In using the zeolite-containing catalyst in the catalytic cyclization reaction, it is preferred to make the zeolite-containing catalyst into a molded body for giving particles of proper shapes. In this case, only the zeolite is molded and the resulting molded body can be used as the zeolite-containing catalyst. However, ordinarily, the zeolite is mixed with a porous refractory inorganic oxide such as alumina, silica, silica/alumina, zirconia, titania, diatomaceous earth, clay or the like as a binder or molding diluent (matrix), the resulting mixture is molded and the resulting molded body is used as the zeolite-containing catalyst.

When the matrix or binder is used, the content thereof is preferably 5-90% by mass, more preferably 10-50% by mass based on the total mass of the zeolite and the matrix or binder.

The conditions of the catalytic cyclization reaction in the present invention varies depending on the hydrocarbon starting material, particularly, the ratio of amount of olefin and paraffin in the starting material, and preferably the temperature is 300-650° C., the partial pressure of the hydrocarbon starting material is 0.01-3 MPa, and the weight hourly space velocity is 0.1-50 $hr^{-1}$, and more preferably the temperature is 400-600° C.

The reaction vessel utilized in the catalytic cyclization reaction of the present invention may be any of fixed bed type, moving bed type and fluidized bed type and the reaction manner is not particularly limited. Preferred is an adiabatic fixed bed type reaction vessel which is simple in structure.

EXAMPLES

The present invention will be explained more specifically by the following examples and comparative examples, which should not be construed as limiting the invention in any manner.

Measurements conducted in the examples and comparative examples are as follows.

(1) Measurement of amount of proton in the zeolite by liquid phase ion exchanging/filtrate titration method.

1.5 g of zeolite was calcined in air at a temperature of 400-600° C., and thereafter subjected to ion exchanging in 25 ml of an aqueous NaCl solution of 3.4 mols/liter while ice cooling for 10 minutes. After the resulting mixture was filtered, the zeolite was washed with 50 ml of pure water, and total amount of the filtrate containing the water used for washing was recovered. This filtrate (containing water used for washing) was subjected to neutralization titration with 0.1N aqueous NaOH solution, and the amount of protons in the zeolite was obtained from the point of neutralization.

(2) Calculation of reaction rate constant K.

The reaction rate constant K ($hr^{-1}$) which is an indication of catalytic activity was obtained by the following formula.

$$K = WHSV \times ln[1/(1-X)]$$

[In the above formula, WHSV ($hr^{-1}$) is the weight hourly space velocity of the fed starting material with respect to the weight of the zeolite, and X (with no unit) is an olefin conversion on the basis of butene {(concentration of olefin of 4-8 carbon atoms in starting material (% by mass)—concentration of butene in product (% by mass)/concentration of olefin of 4-8 carbon atoms in starting material (% by mass)}.

Example 1

An extrusion molded article of H type ZSM-5 having a molar ratio $SiO_2/Al_2O_3$ of 1000 (containing 30% by mass of $SiO_2$ binder and having 1.6 mmφ, and bought from Nikki Universal Co., Ltd.) was dispersed in a 1N aqueous sodium nitrate solution (10 cc/g-zeolite molded body), and ion exchanging treatment was carried out at room temperature for 1 hour repeatedly three times, followed by carrying out filtration, washing with water and drying to prepare an Na type ZSM-5/$SiO_2$. This was dispersed in a 0.01N aqueous silver nitrate solution (10 cc/g-zeolite molded body), and ion exchanging was carried out at room temperature for 2 hours, followed by filtration, washing with water and drying to prepare a catalyst A. The amount of Ag in the catalyst A measured by fluorescent X-ray analysis was 0.15% by mass. The catalyst A was packed in a quartz glass reaction vessel of 16 mmφ in inner diameter and subjected to steaming for 5 hours under the conditions of a temperature of 650° C., a steam flow rate of 27.6 g/hr and a nitrogen flow rate of 140 Ncc/min. The amount of protons in the catalyst A after subjected it to the steaming treatment was measured by liquid phase ion exchanging/filtrate titration method to obtain 0.002 mmol/g. 10 g of the catalyst A after the steaming treatment was packed in a reaction vessel made of HASTELLOY C having an inner diameter of 17 mmφ.

Using C4 raffinate-2 shown in Table 1 (obtained by extracting butadiene and isobutene from a C4 fraction obtained by steam cracking naphtha) as a starting material, a reaction was carried out under the conditions of a reaction temperature of 580° C., a feed amount of the C4 raffinate-2 of 60 g/hr (WHSV=6 $hr^{-1}$) and a pressure of 0.1 MPaG, the resulting reaction product was cooled to about 30° C. at the outlet of the reaction vessel using a heat exchanger and then introduced into a gas-liquid separation drum to separate and recover a liquid (C4+ fraction). The composition of the recovered C4+ fraction is shown in Table 1. Then, using the recovered C4+ fraction and C4 raffinate-2 as starting materials, an experiment of C4+ recycling was carried out for 24 hours under the following experimental conditions.

Experimental conditions:

Reaction temperature: 580° C.; feed rate of C4 raffinate-2: 30 g/hr; feed rate of C4+ fraction: 31.2 g/hr (WHSV=6.1 $hr^{-1}$); reaction pressure: 0.1 MPaG The reaction product obtained after a given time from starting of feeding of starting material was directly introduced into a gas chromatography (TCD, FID detectors) to analyze the composition.

The analysis by gas chromatograph was carried out under the following conditions.

Device: GC-17A manufactured by Shimadzu Corp.

Column: Custom capillary column SPB-1 (0.25 mm in inner diameter, 60 m in length, 3.0 μm in film thickness) manufactured by SUPELCO, Inc.

Amount of sample gas: 1 ml (the sampling line was kept at 200-300° C. to prevent liquefaction).

Heating program: Keeping at 40° C. for 12 minutes, then heating to 200° C. at 5° C./min, and keeping at 200° C. for 22 minutes.

Split ratio: 200:1

Flow rate of carrier gas (nitrogen): 120 ml/min.

FID detector: Air supplying pressure 50 kPa (about 500 ml/min), hydrogen supplying pressure 60 kPa (about 50 ml/min).

Measuring method: TCD detector and FID detector were connected. in series, and hydrogen and hydrocarbons of 1 carbon atom and 2 carbon atoms were detected by the TCD detector and hydrocarbons of 3 or more carbon atoms were detected by the FID detector. After 10 minutes from starting of analysis, the detecting output was switched from TCD to FID.

The results of analysis of the reaction product after 12 hours from starting of the reaction were that yields of propylene and ethylene (% by mass) with respect to the olefin of 4-8 carbon atoms in the feed starting material were 32.1% and 8.7%, respectively. However, the components of 6-8 carbon atoms in the recovered C4+ fraction were all olefins except for aromatic hydrocarbons. Moreover, the ratio of the reaction rate constant K after 4 hours and 24 hours from starting of the reaction [K(24 hours)/K(4 hours)], was 0.90.

Comparative Example 1

The reaction of C4 raffinate-2 was carried out under the same conditions as in Example 1, except that only the C4 raffinate-2 in a feed amount of 60 g/hr (WHSV=6 hr$^{-1}$) was used as a starting material fed to the reaction vessel. The results of analysis of the reaction product after 12 hours from starting of the reaction were that yields of propylene and ethylene (% by mass) with respect to the olefin of 4-8 carbon atoms in the feed starting material were 31.1% and 8.9%, respectively. Moreover, the ratio of the reaction rate constant K after 4 hours and 24 hours from starting of the reaction [K(24 hours)/K(4 hours)], was 0.87.

From the comparison of Example 1 with Comparative Example 1, it can be seen that use of the C4+ fraction, as it is, as a recycling material without removing heavy materials had no adverse effect on deterioration of the catalyst. Furthermore, it can be seen that the non-aromatic components of 6-8 carbon atoms in the C4+ fraction can be effectively utilized for production of propylene and ethylene.

Example 2

An experiment corresponding to recycling of ethylene was conducted under the same conditions as in Example 1, except that the C4 raffinate-2 in an amount of 26.8 g/hr, the C4+ fraction in an amount of 27.2 g/hr, and ethylene in an amount of 6 g/hr (WHSV=6 hr$^{-1}$) were used as the starting materials fed to the reaction vessel.

The results of analysis of the reaction product after 4 hours from starting of the reaction were that yields of propylene and ethylene (% by mass) with respect to the olefin of 4-8 carbon atoms in the feed starting material were 34.8% and 0.5%, respectively. A comparison with Example 1 shows that production of ethylene was suppressed by recycling ethylene and that the yield of propylene was improved.

Example 3

An extrusion molded article of Na type ZSM-5 having a molar ratio $SiO_2/Al_2O_3$ of 1200 (containing 30% by mass of $SiO_2$ binder and having 1.6 mmφ, and bought from Nikki Universal Co., Ltd.) was dispersed in 0.02N aqueous silver nitrate solution (10 cc/g-zeolite molded body), and ion exchange treatment was carried out at 60° C for 1 hour which was repeated two times, followed by carrying out filtration, washing with water and drying to prepare a catalyst B. The amount of Ag in the catalyst B measured by fluorescent X-ray analysis was 0.22% by mass. The catalyst B was packed in a reaction vessel made of HASTELLOY C having an inner diameter of 27 mmφ and subjected to steaming for 5 hours under the conditions of a temperature of 650° C., a steam flow rate of 214 g/hr, a nitrogen flow rate of 400 NL/hr, and a pressure of 0.1 MPaG. The amount of protons in the catalyst B, after the steaming treatment, was measured by liquid phase ion exchanging/filtrate titration method and determined to be 0.002 mmol/g. 60 g of the catalyst B, after the steaming treatment, was packed in a reaction vessel made of HASTELLOY C having an inner diameter of 27 mmφ.

Using C4 raffinate-2 shown in Table 2 as a starting material, a reaction was carried out under the conditions of a reaction temperature of 550° C., a feed amount of the C4 raffinate-2 of 220.2 g/hr, a feed amount of the recycling C4+ fraction of 139.8 g/hr (WHSV=6 hr$^{-1}$), a feed amount of steam of 108 g/hr, and a reaction pressure of 0.1 MPaG, and the resulting reaction product was fed to a distillation column and separated into an $H_2$—C3 fraction and a C4+ fraction. About 56% by mass of the C4+ fraction was recycled to the reaction vessel. After continuing the reaction for 2 days, the catalyst was subjected to regeneration treatment under the following conditions.

Conditions of the regeneration treatment:

Regeneration temperature: 500-550° C.; regeneration pressure: 0.5 MPaG; flow rate of nitrogen+air: 1008 NL/hr; oxygen concentration: 1-5% by volume; regeneration time: 10 hours.

The yields (% by mass) based on the C4 raffinate-2 are shown in Table 2. The ΔAROMA/P was 3.5. The regeneration gas at the outlet of the reaction vessel in the regeneration treatment was periodically sampled and the regeneration gas was analyzed using a gas chromatograph to measure concentrations of $CO_2$ and CO, from which the amount of coke was determined. The amount of coke was divided by the total amount of the starting materials fed during the reaction to obtain a yield of the coke, which was 72 ppm by mass.

Comparative Example 2

The reaction of C4 raffinate-2 was carried out under the same conditions as in Example 3, except that only the C4 raffinate-2 in a feed amount of 360 g/hr (WHSV=6 hr$^{-1}$) was used as a starting material fed to the reaction vessel. The yields (% by mass) based on the C4 raffinate-2 are shown in Table 2. The yield of coke was 77 ppm by mass.

In comparison with Example 3, it can be seen that the yields of ethylene and propylene were improved by recycling the C4+ fraction. Furthermore, it can be seen that the yield of coke did not increase even when the C4+ fraction was recycled as it was.

Example 4

72 parts by mass of H type ZSM-5 (having a molar ratio $SiO_2/Al_2O_3=80$), zinc nitrate (10 parts by mass in terms of zinc metal) and alumina sol (18 parts by mass in terms of $Al_2O_3$) were kneaded and extruded to prepare a molded product of 1.6 mm in diameter and 4-6 mm in length. This was dried at 120° C. for 4 hours and then calcined at 500° C for 3 hours to obtain a ZSM-5 zeolite molded catalyst. This catalyst was dispersed in 1N aqueous sodium nitrate solution (10 cc/g-zeolite molded body), and ion exchange treatment was carried out at room temperature for 1 hour and was repeated three times, followed by filtration, washing with water and drying to prepare an Na-containing ZSM-5/SiO$_2$. This was dispersed in 0.1N aqueous silver nitrate solution (10 cc/g-zeolite molded body), and ion exchange treatment was carried out at room temperature for 2 hours, followed by filtration, washing with water and drying to prepare a catalyst C. The amount of Ag in the catalyst C measured by fluorescent X-ray analysis was 1.8% by weight. The catalyst C was packed in a reaction vessel made of HASTELLOY C having an inner diameter of 27 mmφ and subjected to steaming for 3 hours under the conditions of a temperature of 650° C., a steam flow rate of 214 g/hr, a nitrogen flow rate of 400 NL/hr, and a pressure of 0.1 MPaG. 39.6 g of the catalyst C after the steaming treatment was packed in a reaction vessel made of HASTELLOY C having an inner diameter of 27 mmφ.

A reaction was carried out under the conditions of a feed amount of the C4+ fraction obtained in Example 3 of 110.9 g/hr, a reaction temperature of 515° C. and a pressure of 0.5 MPa. The yield of aromatic hydrocarbon of 6-9 carbon atoms after 2 hours from starting of the reaction was 45.32% by mass. From the results of Example 3 and Example 4, the yields based on the C4 raffinate-2 were 9.08% by mass for ethylene, 38.05% by mass for propylene and 22.82% by mass for aromatic hydrocarbon of 6-9 carbon atoms. Thus, it can be seen that ethylene, propylene and aromatic hydrocarbon of 6-9 carbon atoms are selectively obtained by subjecting the by-product C4+ fraction to a catalytic cyclization reaction.

TABLE 1

[Composition of C4 raffinate-2 and C4+ fraction (% by mass)]

| Components | C4 raffinate-2 | C4+ fraction |
|---|---|---|
| Methylacetylene | 0.07 | 0.00 |
| Propadiene | 0.22 | 0.00 |
| Propylene | 0.18 | 0.01 |
| Propane | 0.04 | 0.00 |
| Butadiene | 1.69 | 0.02 |
| Butene | 78.73 | 7.89 |
| Butane | 17.94 | 4.06 |
| Pentene | 0.30 | 20.47 |
| Pentane | 0.53 | 2.17 |
| Benzene | 0.00 | 2.54 |
| C6 non-aromatic hydrocarbon | 0.00 | 16.15 |
| Toluene | 0.00 | 6.29 |
| C7 non-aromatic hydrocarbon | 0.00 | 16.37 |
| C8 aromatic hydrocarbon | 0.00 | 9.52 |
| C8 non-aromatic hydrocarbon | 0.30 | 7.39 |
| C9+ hydrocarbon | 0.00 | 7.12 |
| Total | 100.00 | 100.00 |

TABLE 2

[Composition of starting material and reaction yield (% by mass)]

| Components | C4 raffinate-2 | Examle 3 (yields) | Comparative Example 2 (yields) |
|---|---|---|---|
| Hydrogen | 0.00 | 0.05 | 0.03 |
| Methane | 0.00 | 0.26 | 0.18 |
| Ethylene | 0.00 | 9.08 | 6.40 |
| Ethane | 0.00 | 0.21 | 0.15 |
| C$_3$H$_4$ | 0.10 | 0.00 | 0.00 |
| Propylene | 0.06 | 38.05 | 26.84 |
| Propane | 0.18 | 1.38 | 1.03 |
| Butadiene | 0.91 | 0.02 | 0.03 |
| Butene | 78.95 | 18.31 | 28.93 |
| Butane | 18.48 | 21.45 | 20.57 |
| Pentene | 0.81 | 6.15 | 9.80 |
| Pentane | 0.35 | 0.40 | 0.38 |
| Benzene | 0.00 | 0.19 | 0.13 |
| C6 non-aromatic hydrocarbon | 0.00 | 1.52 | 2.42 |
| Toluene | 0.00 | 0.63 | 0.46 |
| C7 non-aromatic hydrocarbon | 0.00 | 0.85 | 1.35 |
| C8 aromatic hydrocarbon | 0.00 | 0.64 | 0.45 |
| C8 non-aromatic hydrocarbon | 0.16 | 0.29 | 0.47 |
| C9+ hydrocarbon | 0.00 | 0.52 | 0.38 |
| Total | 100.00 | 100.00 | 100.00 |

INDUSTRIAL APPLICABILITY

According to the production method of the present invention, in the method for producing ethylene and propylene from hydrocarbon starting materials containing olefins, recycling of starting materials is obtained from the reaction product by a simple method. An efficient and stable recycle process can be achieved. Therefore, the method is industrially useful for producing ethylene and propylene.

The invention claimed is:

1. A method of producing ethylene and propylene which comprises contacting a hydrocarbon starting material containing 20% by mass or more of at least one olefin of 4-12 carbon atoms with a catalyst containing a medium pore diameter zeolite, the zeolite containing silver and substantially no protons, having a molar ratio $SiO_2/Al_2O_3$ of 200-5000 and selected from the group consisting of ZSM-5 type zeolites, in a reaction vessel under conditions of a reaction temperature of 400-600° C., a partial pressure of the hydrocarbon starting material of 0.01-0.5 MPa and a weight hourly space velocity of 1-100 hr$^{-1}$ to carry out a catalytic conversion reaction of said at least one olefin of 4-12 carbon atoms, thereby obtaining a reaction mixture containing ethylene and propylene, separating the reaction mixture into a fraction A containing mainly hydrogen and hydrocarbons of 1-3 carbon atoms and a fraction B containing mainly at least one hydrocarbon of 4 or more carbon atoms, and separating ethylene and propylene from the fraction A, said method meeting the following requirements (i) and (ii):

(i) to satisfy $\Delta AROMA/P \leq 13$ $\Delta AROMA = AROMAout - AROMAin$ (AROMAin: percent by mass of aromatic hydrocarbon component of 6-8 carbon atoms in the hydrocarbon starting material at the inlet of the reaction vessel, AROMAout: percent by mass of aromatic hydrocarbon component of 6-8 carbon atoms in the reaction mixture at the outlet of the reaction vessel, P: partial pressure of the hydrocarbon starting material [MPa]); and (ii) to recycle 10-95% by mass of the fraction B to the reaction vessel without removing heavy materials and use it as the hydrocarbon starting material.

2. A method according to claim 1, wherein the fraction A is separated into a fraction $A_1$ containing mainly hydrogen and hydrocarbons of 1-2 carbon atoms and a fraction $A_2$ containing mainly hydrocarbons of 3 carbon atoms, and at least a part of the fraction $A_1$ is recycled to the reaction vessel and used as a part of the hydrocarbon starting material.

3. A method according to claim 1, wherein 15-90% by mass of the fraction B is recycled to the reaction vessel and used as a part of the hydrocarbon starting material.

4. A method according to claim 1, wherein the formula in the requirement (i) is $\beta AROMA/P \leq 10$.

5. A method of producing ethylene and propylene which comprises contacting a hydrocarbon starting material containing 20% by mass or more of at least one olefin of 4-12 carbon atoms with a catalyst containing a medium pore diameter zeolite, the zeolite containing silver and substantially no protons, having a molar ratio $SiO_2/Al_2O_3$ of 200-5000 and selected from the group consisting of ZSM-5 type zeolites, in a reaction vessel under the conditions of a reaction temperature of 400-600° C., a partial pressure of the hydrocarbon starting material of 0.01-0.5 MPa and a weight hourly space velocity of 1-100 $hr^{-1}$ to carry out a catalytic conversion reaction of said at least one olefin of 4-12 carbon atoms, thereby obtaining a reaction mixture containing ethylene and propylene, separating the reaction mixture into a fraction C containing mainly hydrogen and hydrocarbons of 1-2 carbon atoms and a fraction D containing mainly at least one hydrocarbon of 3 or more carbon atoms, separating the fraction D into a fraction $D_1$ containing mainly a hydrocarbon of 3 carbon atoms and a fraction $D_2$ containing mainly at least one hydrocarbon of 4 or more carbon atoms, and separating ethylene and/or propylene from the fraction C and/or the fraction $D_1$, said method meeting the following requirements (i) and (ii):

(i) to satisfy $\Delta AROMA/P \leq 13$ $\Delta AROMA = AROMAout - AROMAin$ (AROMAin: percent by mass of aromatic hydrocarbon component of 6-8 carbon atoms in the hydrocarbon starting material at the inlet of the reaction vessel, AROMAout: percent by mass of aromatic hydrocarbon component of 6-8 carbon atoms in the reaction mixture at the outlet of the reaction vessel, P: partial pressure of the hydrocarbon starting material [MPa]); and (ii) to recycle 10-95% by mass of the fraction $D_2$ to the reaction vessel without removing heavy materials and use it as the hydrocarbon starting material.

6. A method according to claim 5, wherein at least a part of the fraction C is recycled to the reaction vessel and used as a part of the hydrocarbon starting material.

7. A method according to claim 5, wherein 15-90% by mass of the fraction $D_2$ is recycled to the reaction vessel and used as the hydrocarbon starting material.

8. A method according to claim 5, wherein the formula in the requirement (i) is $\Delta AROMA/P \leq 10$.

9. A method according to any one of claims 1-8, wherein the reaction vessel is an adiabatic fixed bed reaction vessel.

10. A method according to any one of claims 1-8, wherein the reaction temperature is 500-580° C., the partial pressure of the hydrocarbon starting material is 0.05-0.3 MPa and the weight hourly space velocity is 2-10 $hr^{-1}$.

11. A method according to any one of claims 1-4, wherein a part of the fraction B is used as a part or all of the hydrocarbon starting material and is contacted with a medium pore diameter zeolite-containing catalyst containing at least one member selected from the group consisting of metals belonging to Group IIB, Group IIIB and Group VIII of the periodic table and compounds thereof at a temperature of 650° C. or less in a gaseous phase to obtain an aromatic hydrocarbon.

12. A method according to claim 11, wherein in the case of using a part of the fraction B as a part of the hydrocarbon starting material, the fraction $A_1$ containing mainly hydrogen and hydrocarbons of 1-2 carbon atoms which is separated from the fraction A is additionally used as a part of the hydrocarbon starting material.

13. A method according to any one of claims 5-8, wherein a part of the fraction $D_2$ is used as a part or all of the hydrocarbon starting material and is contacted with a medium pore diameter zeolite-containing catalyst containing at least one selected from the group consisting of metals belonging to Group IIB, Group IIIB and Group VIII of the periodic table and compounds thereof at a temperature of 650° C. or less in a gaseous phase to obtain an aromatic hydrocarbon.

14. A method according to claim 13, wherein in the case of using a part of the fraction $D_2$ as a part of the hydrocarbon starting material, the fraction C is additionally used as a part of the hydrocarbon starting material.

* * * * *

UNITED STATES PATENT AND TRADEMARK OFFICE
CERTIFICATE OF CORRECTION

PATENT NO. : 7,754,934 B2
APPLICATION NO. : 11/631644
DATED : July 13, 2010
INVENTOR(S) : Takashi Tsunoda et al.

Page 1 of 1

It is certified that error appears in the above-identified patent and that said Letters Patent is hereby corrected as shown below:

IN THE CLAIMS:

In claim 4, at column 21, line 16, change "βAROMA/P≤10" to --ΔAROMA/P≤10--.

Signed and Sealed this
Twentieth Day of August, 2013

Teresa Stanek Rea
*Acting Director of the United States Patent and Trademark Office*